United States Patent
Ruoslahti et al.

(10) Patent No.: US 7,745,410 B2
(45) Date of Patent: Jun. 29, 2010

(54) BLADDER TUMOR-TARGETING PEPTIDE AND USE THEREOF

(75) Inventors: Erkki Ruoslahti, La Jolla, CA (US); Byung-Heon Lee, Daegu (KR); In-San Kim, Daegu (KR)

(73) Assignees: Kyungpook National University Industry-Academica Cooperation Foundation, Daegu (KR); Burnham Institute for Medical Research, La Jolla, CA (US)

( * ) Notice: Subject to any disclaimer, the term of this patent is extended or adjusted under 35 U.S.C. 154(b) by 114 days.

(21) Appl. No.: 11/979,624

(22) Filed: Nov. 6, 2007

(65) Prior Publication Data

US 2008/0139479 A1    Jun. 12, 2008

Related U.S. Application Data

(60) Provisional application No. 60/856,785, filed on Nov. 6, 2006.

(51) Int. Cl.
*A61K 38/08* (2006.01)
*A61K 39/395* (2006.01)

(52) U.S. Cl. .................................. 514/15; 424/155.1
(58) Field of Classification Search .................. None
See application file for complete search history.

(56) References Cited

U.S. PATENT DOCUMENTS 6,358,920 B1 *   3/2002   Blaschuk et al. ............... 514/9

\* cited by examiner

*Primary Examiner*—Andrew D Kosar
*Assistant Examiner*—Satyanarayana R Gudibande
(74) *Attorney, Agent, or Firm*—Buchanan Ingersoll & Rooney PC

(57) ABSTRACT

The present invention relates to a bladder tumor-targeting peptide and use thereof. More particularly, the present invention relates to a bladder tumor-targeting peptide having an amino acid sequence represented by SEQ ID NO: 7 and use thereof. The peptide according to the present invention is capable of specific binding to bladder tumor cells in vivo and in vitro. The peptide according to the present invention or an antibody thereof is useful for a marker for the diagnosis of bladder tumors, and for a drug carrier targeting bladder tumor.

8 Claims, 7 Drawing Sheets
(5 of 7 Drawing Sheet(s) Filed in Color)

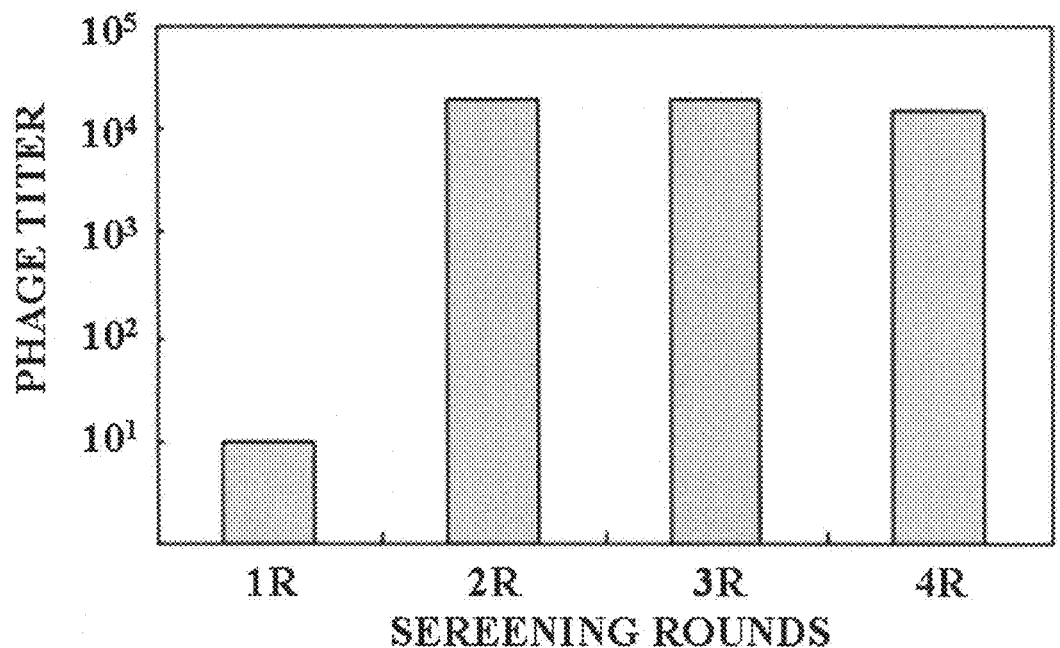

PEPTIDE 1: (AMINO TERMINAL) CSNRDARRC (CARBOXYL TERMINAL) : SEQ. ID NO. 1
PEPTIDE 2: (AMINO TERMINAL) CPNGDERNC (CARBOXYL TERMINAL) : SEQ. ID NO. 2
PEPTIDE 3: (AMINO TERMINAL) CANKDVRRC (CARBOXYL TERMINAL): SEQ. ID NO. 3
PEPTIDE 4: (AMINO TERMINAL) CPNQDSRRC (CARBOXYL TERMINAL): SEQ. ID NO. 4
PEPTIDE 5: (AMINO TERMINAL) CVNNDGRLC (CARBOXYL TERMINAL): SEQ. ID NO. 5
PEPTIDE 6: (AMINO TERMINAL) CANLDTRRC (CARBOXYL TERMINAL): SEQ. ID NO. 6
CONSENSUS SEQUENCE: (AMINO TERMINAL) CXNXDXRXC (CARBOXYL TERMINAL) : SEQ. ID NO. 7

BLADDER TUMOR-TARGETING PEPTIDE AND USE THEREOF

RELATED APPLICATIONS

This application claims the benefit of U.S. Provisional Application No. 60/856,785, filed Nov. 6, 2006, the disclosures of which is incorporated herein by reference in its entirety.

FIELD OF THE INVENTION

The present invention relates to a bladder tumor-targeting peptide and use thereof. More particularly, the present invention relates to a bladder tumor-targeting peptide having an amino acid sequence represented by SEQ ID NO: 7 and use thereof.

BACKGROUND OF THE INVENTION

The bladder is an internal organ located in the pelvis, and serves as a kind of pouch, in which urine is stored temporarily after it is made in the kidney and then transported via the pelvis of the kidney and the ureter. If the bladder expands due to the urine stored therein, one feels a need to urinate and then passes urine. Upon passing urine, muscles of the bladder shrink to discharge urine completely. The surface of the bladder is covered with an epithelium referred to as the transitional epithelium, and is characterized by showing excellent elasticity. The bladder tumor occurs during the conversion of the transitional epithelium into a tumor. Most bladder tumors (90% or more) are transitional epithelial cell carcinomas. In Korea, bladder tumors are the most frequent among cancers occurring in the urinogenital organs. The incidence of bladder cancer is 7.76 per 100,000 for man and 1.19 per 100,000 for woman. In Korea, bladder tumors are the fourth occurring cancer in man. Actually, about 70% of bladder tumors are superficial, 20% thereof are invasive only to the bladder, and 10% thereof are metastatic. About 70% of superficial bladder tumors are recurred, wherein most of recurred bladder tumors are superficial, and 10-15% thereof proceeds into invasive or metastatic bladder tumors. About 30% of superficial bladder tumors are not recurred and have no problem in convalescence. However, 10-15% of superficial bladder tumors occasionally proceed into invasive or metastatic tumors despite of various therapies.

Heretofore, diagnosis of a bladder tumor has been performed by cytology of bladder, which comprises staining cells separated from urine via a Pap (Papanicolau) staining method and observing the shape of each cell with a microscope to screen a tumor cell, and by endoscopy of bladder, which comprises screening a tumor directly inside bladder through an endoscope. The cytology has an advantage of a correct diagnosis of a tumor cell, once the tumor cell is found, while having disadvantages of a great possibility of failing to notice tumor cells and time-consuming. On the other hand, the endoscopy of bladder has a disadvantage of putting subject into inconvenience while inserting an endoscope into the bladder through urethra. Therefore, it is necessary to provide a novel diagnosis method that solves the aforementioned problems occurring in the prior art, and a diagnosis system that can be used for the same diagnosis method.

Meanwhile, drug delivery systems or targeting therapies, by which drugs are delivered selectively to tumors, are interested. This is because drug delivery systems or the targeting therapies can provide an increased drug efficacy under the same amount of an anti-tumor agent, and significantly reduced side effects adversely affecting normal tissue. Additionally, when such systems or therapies are applied to gene therapy, it is possible to increase the efficiency of treatment and to reduce serious side effects by virtue of the selective delivery of virus to tumor cells. For this, many attempts have been made to develop an antigen specific to a tumor cell and an antibody for targeting the antigen. However, such antibody has problems of possibility of immune responses and a low tissue-infiltration efficiency. On the other hand, peptides have a low molecular weight, and thus having low possibility of immune responses and high tissue-infiltration efficiency. Therefore, the combination of a tumor-targeting peptide with a conventional anti-tumor agent can provide an intelligent drug carrier capable of selective drug delivery to a tumor. Under these circumstances, there has been a continuous need to develop a novel tumor-targeting peptide.

SUMMARY OF THE INVENTION

In view of the above-mentioned problems occurring in the prior art, the present inventors have conducted intensive studies to develop a bladder tumor-targeting peptide that can be used for the diagnosis of a bladder tumor. We have screened peptides specific to a bladder tumor cell by using phage peptide display technique and have found that such peptides could be used as diagnosis markers and intelligent drug carriers for the bladder tumor. The present invention is based on this finding.

Therefore, an object of the present invention is to provide a bladder tumor-targeting peptide and use thereof.

BRIEF DESCRIPTION OF THE DRAWINGS

The application file contains at least one drawing executed in color. Copies of this patent application with the color drawings will be provided by the Office upon request and payment of the necessary fees.

The foregoing and other objects, features and advantages of the present invention will become more apparent from the following detailed description when taken in conjunction with the accompanying drawings in which:

FIG. 1 shows the results for screening phages capable of specific binding to bladder tumor cells by using phage peptide display technique after four screening rounds, wherein the transverse axis represents a screening round and the longitudinal axis represents a phage titer (transforming unit$\times 10^{-3}$);

FIG. 2 shows amino acid sequences of typical six bladder tumor cell-targeting peptides that are screened by phage peptide display technique, and the common pattern thereof, wherein the common pattern is expressed by bold letters;

Figure 5:
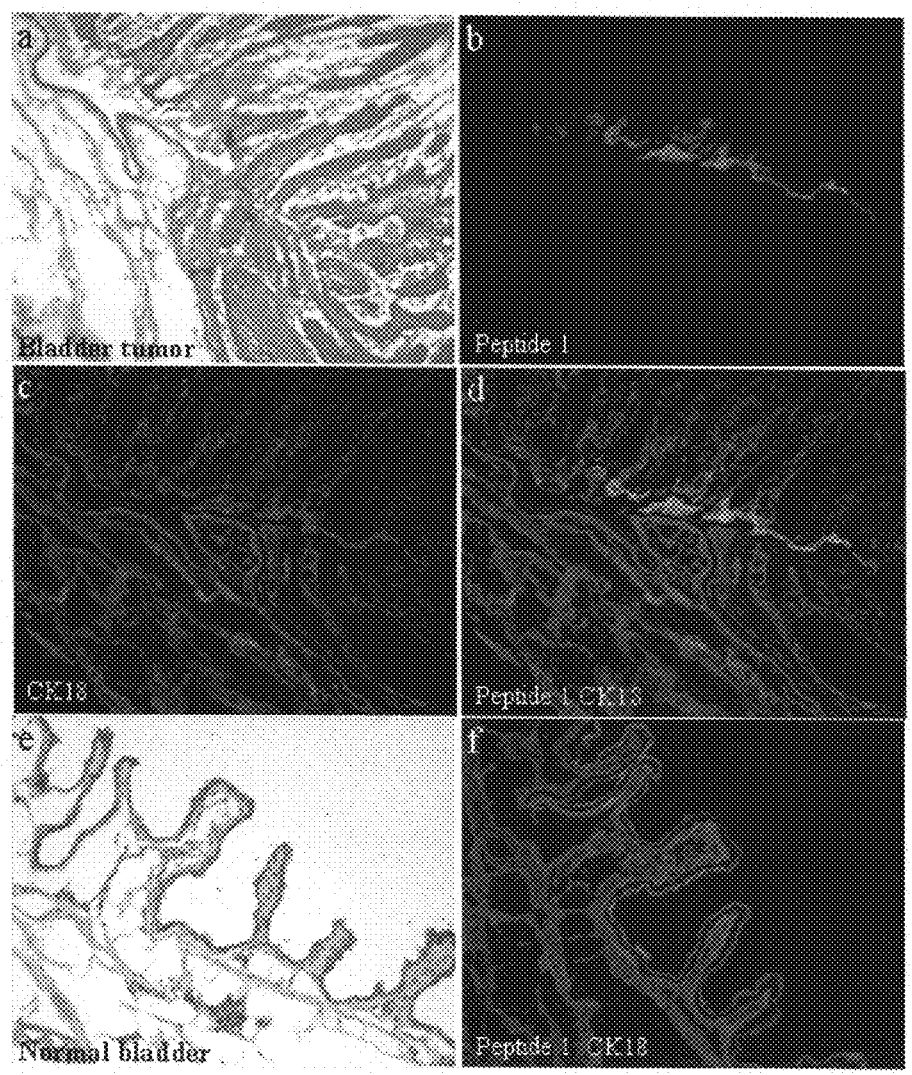
Figure 6:
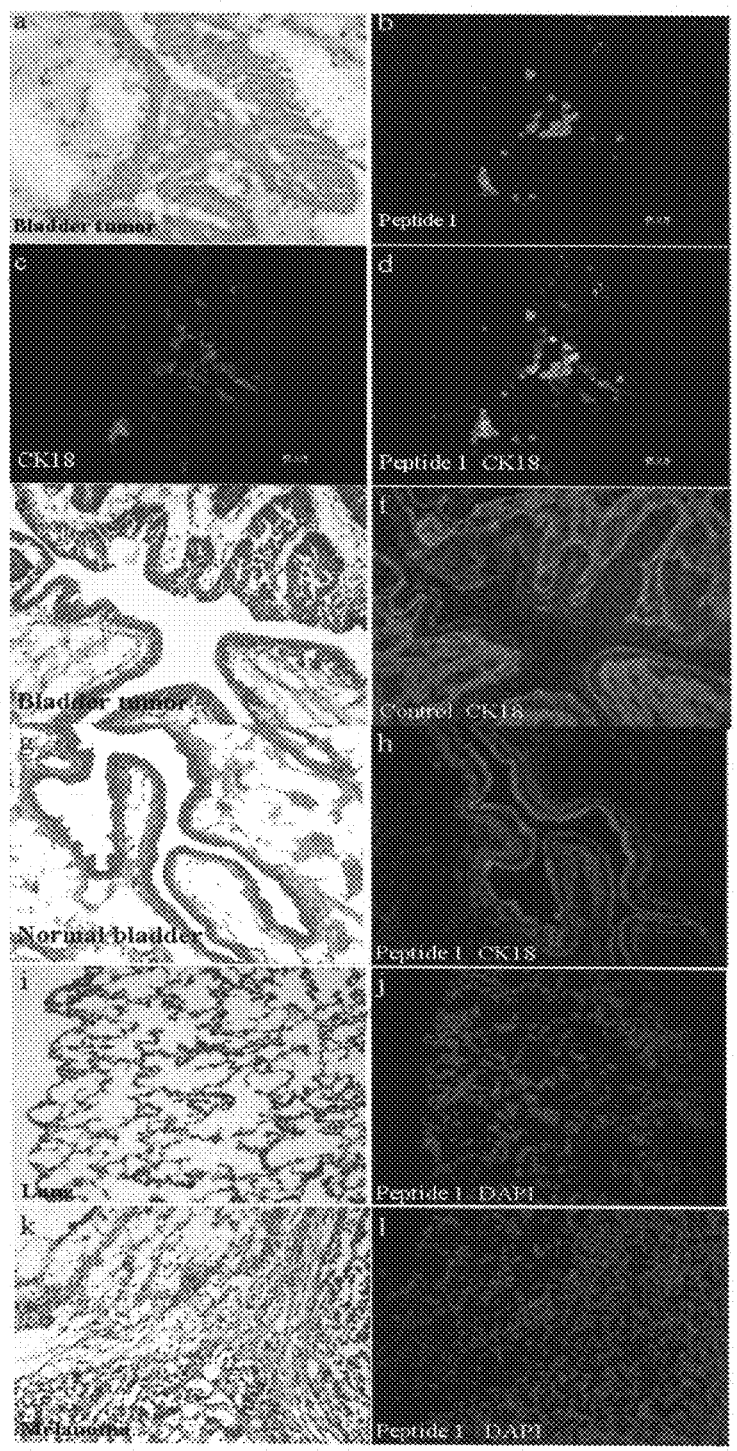
Figure 7:
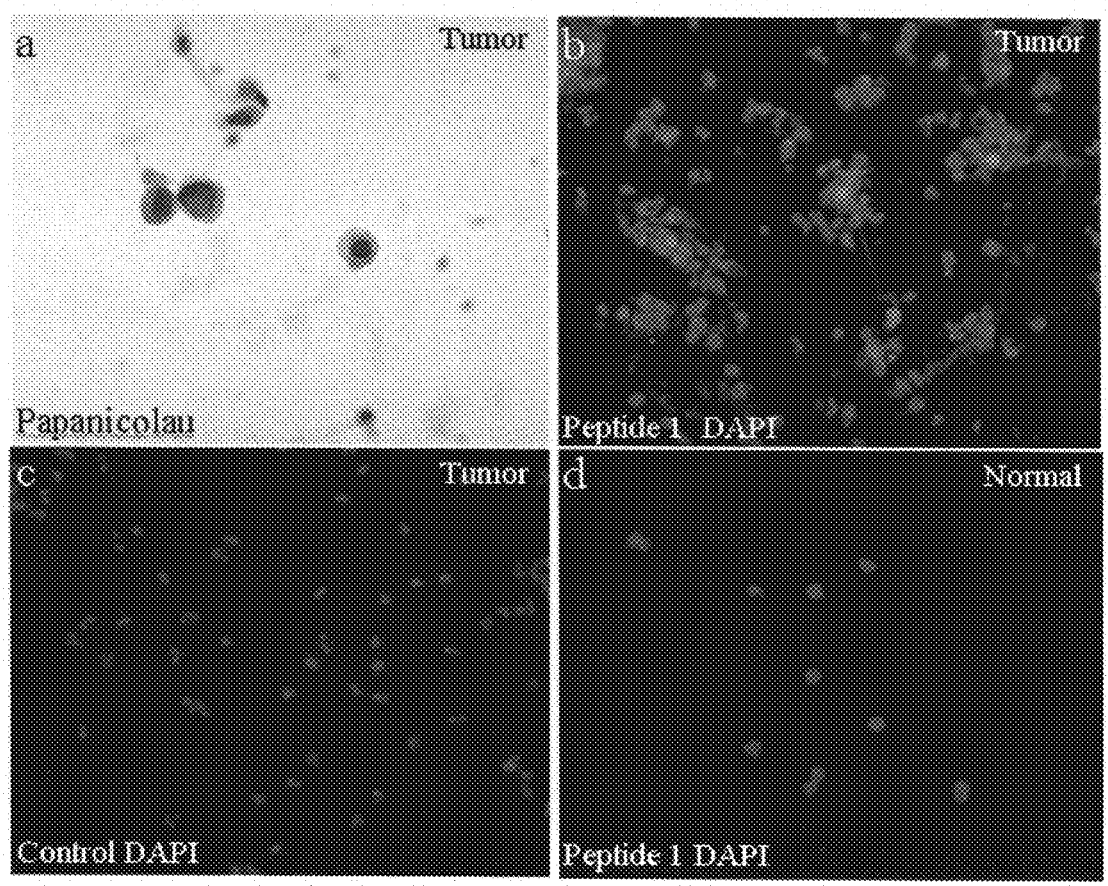

a: microscopic photograph of bladder tumor tissue stained with H & E;

b: fluorescence microscopic photograph of stained bladder tumor tissue, which has reacted with the peptide according to the present invention and then, stained with DAPI;

c: fluorescence microscopic photograph of stained bladder tumor tissue, which has reacted with the control peptide and then, stained with DAPI;

d: microscopic photograph of normal bladder tissue stained with H & E;

e: fluorescence microscopic photograph of stained normal bladder tissue, which has reacted with the peptide according to the present invention and then, stained with DAPI;

f: fluorescence microscopic photograph of stained normal bladder tissue, which has reacted with the control peptide and then, stained with DAPI;

g: microscopic photograph of lung cancer tissue stained with H & E; and h: fluorescence microscopic photograph of stained lung cancer tissue, which has reacted with the peptide according to the present invention and then, stained with DAPI;

FIG. 5 is a set of photographs showing the binding specificity to bladder tumor tissue of the peptide according to the present invention having FITC attached thereto, after injecting the peptide into the mouse bladder in which a bladder tumor is induced, wherein the green fluorescence represents the peptide according to the present invention, and the red fluorescence represents an epithelial cell stained with cytokeratin;

a: microscopic photograph of mouse bladder tumor tissue, injected with the peptide according to the present invention and stained with H & E;

b: fluorescence microscopic photograph of mouse bladder tumor tissue injected with the peptide according to the present invention;

c: microscopic photograph of mouse bladder tumor tissue injected with the peptide according to the present invention and stained with a CK18 antibody;

d: photograph obtained by merging photograph b with photograph c by computer imaging;

e: microscopic photograph of normal bladder tissue of a mouse as a control, injected with the peptide according to the present invention and stained with H & E;

f: photograph obtained by merging a fluorescence microscopic photograph of normal bladder tissue of a mouse as a control, injected with the peptide according to the present invention with a photograph of the normal bladder tissue stained with a CK18 antibody, by computer imaging;

FIG. 6 is a set of photographs showing the in vivo targeting capability of the peptide according to the present invention, after injecting the peptide having FITC attached thereto into the tail venous vessel of a mouse in which a bladder tumor is induced, wherein the green fluorescence represents the peptide according to the present invention, and the red fluorescence represents an epithelial cell stained with cytokeratin;

a: microscopic photograph of mouse bladder tumor tissue injected with the peptide according to the present invention and stained with H & E;

b: fluorescence microscopic photograph of mouse bladder tumor tissue injected with the peptide according to the present invention;

c: microscopic photograph of bladder tumor tissue injected with the peptide according to the present invention and stained with a CK18 antibody;

d: photograph obtained by merging photograph b with photograph c by computer imaging;

e: microscopic photograph of bladder tumor tissue of a mouse, injected with a control peptide and stained with H & E;

f: photograph obtained by merging a fluorescence microscopic photograph of bladder tumor tissue injected with control peptide with a photograph of the bladder tumor tissue stained with cytokeratin, by computer imaging;

g: microscopic photograph of normal bladder tissue of a mouse as a control, injected with the peptide according to the present invention and stained with H & E;

h: photograph obtained by merging a fluorescence microscopic photograph of normal bladder tissue of a mouse as a control, injected with the peptide according to the present invention with a photograph of normal bladder tissue stained with a CK18 antibody, by computer imaging;

i: microscopic photograph of mouse lung tissue injected with the peptide according to the present invention and stained with H & E;

j: fluorescence microscopic photograph of mouse lung tissue injected with the peptide according to the present invention and stained with DAPI;

k: microscopic photograph of malignant melanoma of mouse injected with the peptide according to the present invention and stained with H & E; and l: fluorescence microscopic photograph of cancer tissue of mouse injected with the peptide according to the present invention and stained with DAPI; and FIG. 7 is a set of fluorescence microscopic photographs showing the binding specificity of the target peptide having FITC attached thereto to cells separated from the urine of a patient suffering from bladder tumor, wherein the green fluorescence represents the peptide according to the present invention, and the blue fluorescence represents the nucleus stained with DAPI;

a: microscopic photograph showing bladder tumor cells, stained by PAP (papanicolau) staining method;

b: microscopic photograph showing bladder cells separated from the patient's urine, and reacted with the peptide according to the present invention;

c: microscopic photograph showing bladder cells separated from the patient's urine, and reacted with the control peptide; and d: microscopic photograph showing bladder cells separated from the normal human urine, and reacted with the peptide according to the present invention.

Figure 8:
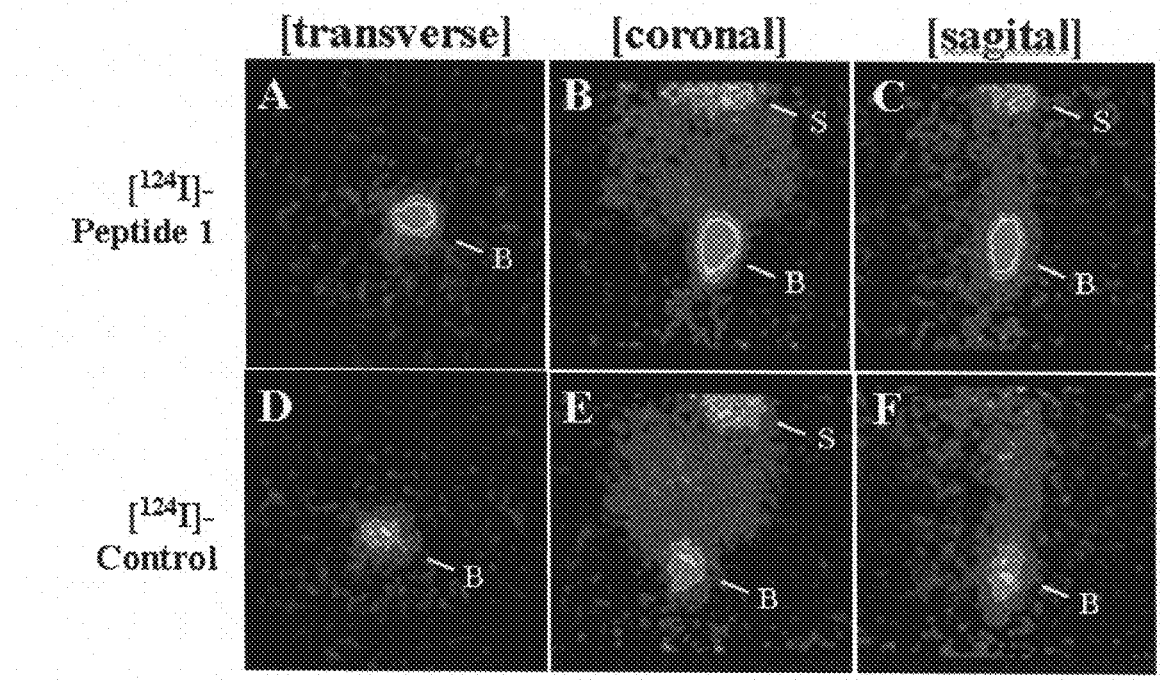

FIG. 8 shows in vivo micro PET (positron emission tomography) images taken at 14 hours after intravenous injection of radiolabeled peptides into rats bearing BBN-induced bladder tumor (B, bladder; S, stomach);

a: transverse view of micro PET images in rats injected with [$^{124}$I]-labeled CSNRDARRC peptide b: coronal view of micro PET images in rats injected with [$^{124}$I]-labeled CSNRDARRC peptide c: sagital view of micro PET images in rats injected with [$^{124}$I]-labeled CSNRDARRC peptide d: transverse view of micro PET images in rats injected with [$^{124}$I]-labeled CDASRRNRC control peptide e: coronal view of micro PET images in rats injected with [$^{124}$I]-labeled CDASRRNRC control peptide f: sagital view of micro PET images in rats injected with [$^{124}$I]-labeled CDASRRNRC control peptide.

DETAILED DESCRIPTION OF THE INVENTION

To accomplish the object of the present invention, the present invention provides a peptide having an amino acid sequence represented by SEQ ID NO: 7 and an antibody thereof.

To accomplish another object of the present invention, the present invention provides a kit for diagnosis of a bladder tumor, which comprises the peptide.

To accomplish still another object of the present invention, the present invention provides a drug delivery composition comprising the peptide.

Hereinafter, the present invention will be described in more detail.

The present invention provides a novel bladder tumor-targeting peptide. The peptide according to the present invention has an amino acid sequence comprising 9 amino acids of CXNXDXRXC (SEQ ID NO: 7). The invention further provides an isolated peptide or peptidomimetic containing the amino acid sequence CXNXDXRXC (SEQ ID NO: 7) or a peptidomimetic thereof. In the amino acid sequence represented by SEQ ID NO: 7, X means an arbitrary amino acid. Preferably, the second amino acid (X) is any one selected from the group consisting of serine (S), proline (P), alanine (A) and valine (V), and the fourth amino acid (X) is any one selected from the group consisting of arginine (R), glycine (G), lysine (K), glutamine (Q), asparagine (N) and leucine (L). Also, preferably, the sixth amino acid (X) is any one selected from the group consisting of alanine (A), glutamic acid (E), valine (V), serine (S), glutamine (G) and threonine (T), and the eighth amino acid (X) is any one selected from the group consisting of arginine (R), asparagine (N) and leucine (L). More preferably, the peptide according to the present invention may have amino acid sequences represented by SEQ ID NO: 1 to SEQ ID NO: 6. The peptide according to the present invention is characterized in that it is capable of specific binding to a bladder tumor cell, in vivo or in vitro. A peptide or peptidomimetic of the invention can be, for example, cyclic or otherwise conformationally constrained and can have a variety of lengths, for example, a length of less than 100 residues, a length of less than 50 residues, a length less than 20 residues, or a length of less than 15 residues. In one embodiment, a peptide or peptidomimetic of the invention which contains the amino acid sequence CXNXDXRXC (SEQ ID NO: 7), or a peptidomimetic of one of these sequences, has cytotoxic activity. It is understood that a peptide containing, for example, the amino acid sequence SEQ ID NO: 7 includes the specified amino acids as a contiguous sequence in which the specified amino acids are not separated by other amino acids.

Figure 3:
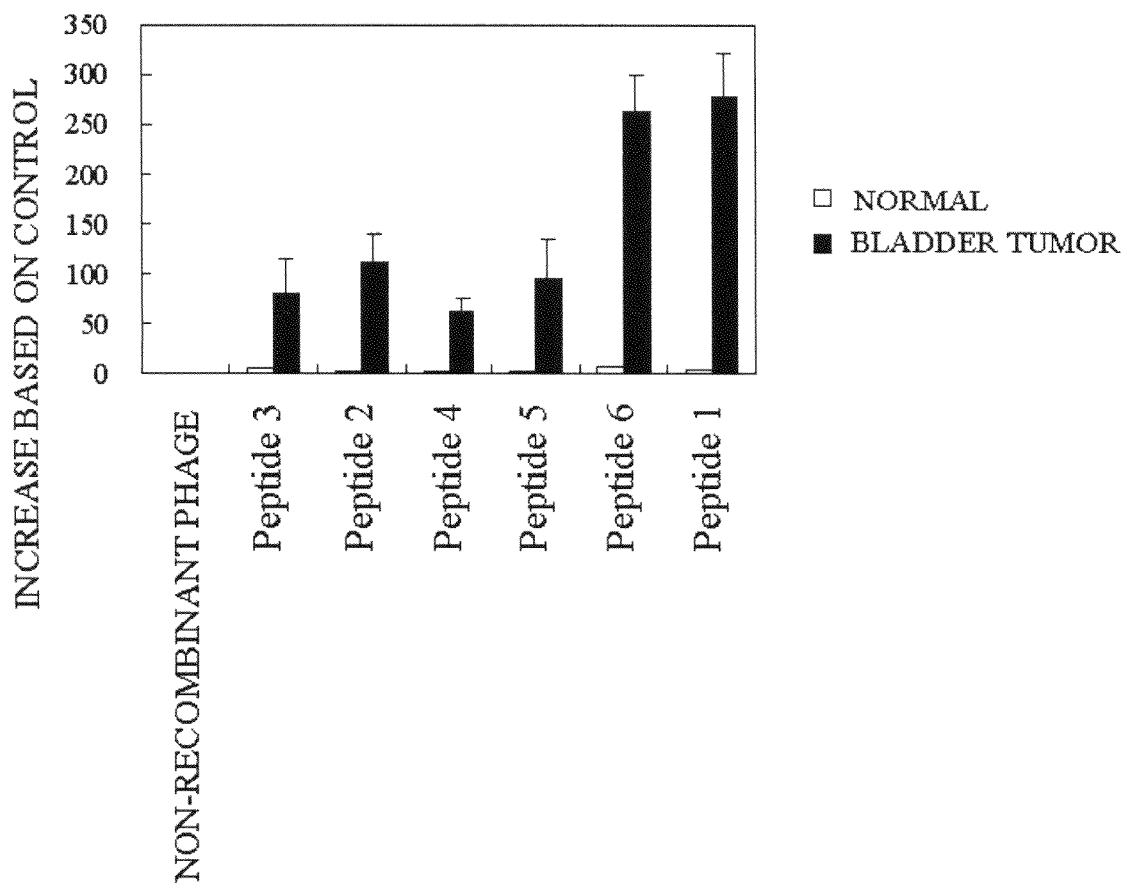
FIG. 3 is a graph showing the binding specificity of six positive phage clones to the bladder tumor cells separated from the human bladder tissue and to the normal bladder cells.
Figure 4:
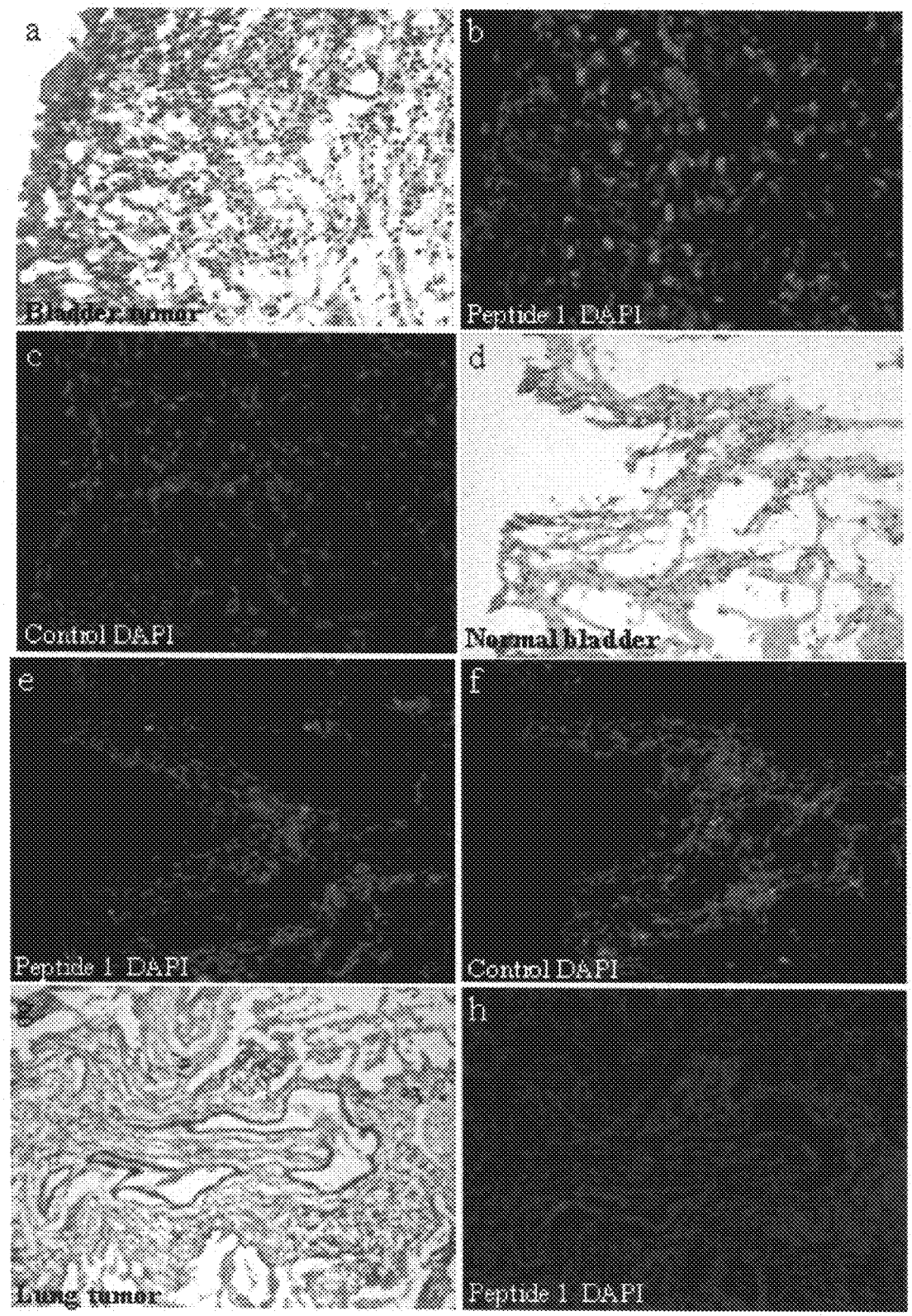
FIG. 4 is a set of photographs showing the binding specificity to the frozen section of human bladder tumor cells of the peptide according to the present invention having FITC attached thereto, wherein the green fluorescence represents the peptide according to the present invention, and the blue fluorescence represents the nucleus stained with DAPI.

In one embodiment of the present invention, it was shown that the peptide according to the present invention, screened by phage peptide display technique, is capable of specific binding to a bladder tumor tissue and bladder cell obtained from a patient with a bladder tumor (see FIGS. 3 and 4). In another embodiment of the present invention, the peptide according to the present invention was injected into the bladder tissue of a mouse with a bladder tumor via the urethra and veins to examine whether the peptide is capable of in vivo targeting of bladder tumor cells using a fluorescence microscope and PET (positron emission tomography). As a result, the peptide according to the present invention is capable of specific binding to the epithelial tissue at the site, where a bladder tumor is induced (see FIGS. 5, 6 and 8).

Additionally, in still another embodiment of the present invention, the peptide according to the present invention was allowed to react with each of the bladder cells obtained from the urine of a patient with a bladder tumor or that of a normal human. As a result, the peptide according to the present invention is capable of specific binding to a bladder tumor cell (see FIG. 7).

The peptides and peptidomimetics of the invention are provided in isolated form. As used herein in reference to a peptide or peptidomimetic of the invention, the term "isolated" means a peptide or peptidomimetic that is in a form that is relatively free from material such as contaminating polypeptides, lipids, nucleic acids and other cellular material that normally is associated with the peptide or peptidomimetic in a cell or that is associated with the peptide or peptidomimetic in a library or in a crude preparation. The peptides and peptidomimetics of the invention, including the bifunctional, multivalent and homing peptides and peptidomimetics discussed below, can have a variety of lengths. A peptide or peptidomimetic of the invention can have, for example, a relatively short length of less than eight, nine, ten, 12, 15, 20, 25, 30, or 40 residues. A peptide or peptidomimetic of the invention also can be useful in the context of a significantly longer sequence. For example, as disclosed herein, CXNXDXRXC (SEQ ID NO: 7), maintained the ability to home when fused to a phage coat protein, confirming that a peptide of the invention can have selective homing activity when embedded in larger protein sequence. Thus, a peptide or peptidomimetic of the invention can have, for example, a length of up to 50, 100, 150 or 200 residues. As used herein, the term "residue" refers to amino acids or analogs thereof.

The present invention also provides an isolated peptide or peptidomimetic containing the amino acid sequence CXNXDXRXC (SEQ ID NO: 7) or any one the amino sequence selected from the group consisting of amino acid sequences represented by SEQ ID NO: 1 to SEQ ID NO: 6, or a conservative variant or peptidomimetic of one of these sequences. As used herein, a "conservative variant" is an amino acid sequence in which a first amino acid is replaced by a second amino acid or amino acid analog having at least one similar biochemical property, which can be, for example, similar size, charge, hydrophobicity or hydrogen-bonding capacity. For example, a first hydrophobic amino acid can be conservatively substituted with a second (non-identical) hydrophobic amino acid such as alanine, valine, leucine, or isoleucine, or an analog thereof. Similarly, a first basic amino acid can be conservatively substituted with a second basic amino acid such as arginine or lysine, or an analog thereof. In the same way, a first acidic amino acid can be conservatively substituted with a second acidic amino acid such as aspartic acid or glutamic acid, or an analog thereof, or an aromatic amino acid such as phenylalanine can be conservatively substituted with a second aromatic amino acid or amino acid analog, for example, tyrosine.

The invention further provides a chimeric protein containing a peptide or peptidomimetic of the invention, or a homing peptide or peptidomimetic of the invention, fused to a heterologous protein. In one embodiment, the invention provides a chimeric protein containing a homing peptide or peptidomimetic that selectively homes to bladder tumor fused to a heterologous protein. The term "heterologous," as used herein in reference to a protein fused to a peptide or peptidomimetic of the invention, means a protein derived from a source other than the gene encoding the peptide of the invention or upon which the peptidomimetic is derived. A chimeric protein of the invention can have a variety of lengths, for example, up to 100, 200, 300, 400, 500 or 800 residues.

As used herein, the term "peptide" is used broadly to mean peptides, proteins, fragments of proteins and the like. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids and have an activity such as selective homing activity of the peptide upon which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803 861).

A variety of peptidomimetics are known in the art including, for example, peptide-like molecules which contain a constrained amino acid, a non-peptide component that mimics peptide secondary structure, or an amide bond isostere. A peptidomimetic which mimics peptide secondary structure can contain. A peptidomimetic also can be a peptide-like molecule which contains, for example, an amide bond isostere such as a retro-inverso modification; reduced amide bond; methylenethioether or methylenesulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). This structural depository is continually updated as new crystal structures are determined and can be screened for compounds having suitable shapes, for example, the same shape as a peptide of the invention, as well as potential geometrical and chemical complementarity to a target molecule. Where no crystal structure of a peptide of the invention or a target molecule that binds the peptide is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of a peptide of the invention, for example, with activity in selectively homing to bladder tumor.

An isolated peptide or peptidomimetic of the invention, or a homing molecule of the invention as discussed further below, can be cyclic, or otherwise conformationally constrained. As used herein, a "conformationally constrained" molecule, such as a peptide or peptidomimetic, is one in which the three-dimensional structure is maintained substantially in one spatial arrangement over time. Conformationally constrained molecules can have improved properties such as increased affinity, metabolic stability, membrane permeability or solubility. Methods of conformational constraint are well known in the art and include cyclization.

In one embodiment, a peptide or peptidomimetic of the invention, or a homing molecule such as a homing peptide or peptidomimetic, is cyclic. As used herein, the term "cyclic" refers to a molecule having non-adjacent components linked to one another through a covalent or ionic bond or through an equivalent interaction such that a rigid or semi-rigid three dimensional structure of the molecule is maintained.

As used herein in reference to a peptide or peptidomimetic, the term cyclic refers to a structure including an intramolecular bond between two non-adjacent amino acids or amino acid analogues. The cyclization can be affected through a covalent or non-covalent bond. Intramolecular bonds include, but are not limited to, backbone to backbone, side-chain to backbone and side-chain to side-chain bonds. A preferred method of cyclization is through formation of a disulfide bond between the side-chains of non-adjacent amino acids or amino acid analogs.

The invention also provides a conjugate which contains a moiety linked to a molecule that specifically binds the receptor bound by peptide SEQ ID NO: 7 and that selectively homes to bladder tumor. In such a conjugate, the molecule can be, for example, a peptide or peptidomimetic, and the moiety can be any of the moieties disclosed herein as useful in the conjugates of the invention.

As used herein, the term "molecule" is used broadly to mean a polymeric or non-polymeric organic chemical such as a small molecule drug; a nucleic acid molecule such as an RNA, a cDNA or an oligonucleotide; a peptide or peptidomimetic; or a protein such as an antibody or a growth factor receptor or a fragment thereof such as an Fv, Fd, or Fab fragment of an antibody containing the antigen-binding domain.

In another embodiment, the peptide or peptidomimetic portion of the conjugate has a defined length. The peptide or peptidomimetic portion of the conjugate can have, for example, a length of at most 10, 20, 30, 40, 50, 100, 150, 200, 250, 300, 400, 500, 600, 700, 800, 900, 1000 or 2000 residues. It is understood that the term "peptide or peptidomimetic portion of the conjugate" means total number of residues in the homing peptide or peptidomimetic and any contiguous protein, peptide or peptidomimetic, such as a therapeutic protein or pro-apoptotic peptide.

The peptide according to the present invention may be prepared with ease by chemical synthetic processes known to one skilled in the art (Creighton, Proteins; Structures and Molecular Principles, W. H. Freeman and Co., NY, 1983). Typical examples of such processes include, but are not limited to, liquid or solid phase synthesis, fragment condensation, F-MOC or T-BOC chemistry (Chemical Approaches to the Synthesis of Peptides and Proteins, Williams et al., Eds., CRC Press, Boca Raton Fla., 1997: A Practical Approach, Athert on & Sheppard, Eds., IRL Press, Oxford, England, 1989).

Additionally, the peptide according to the present invention may be prepared by a genetic engineering method. First, a DNA nucleotide encoding the peptide is constructed by a conventional method. The construction of the DNA nucleotide may be performed by PCR amplification using a suitable primer. Otherwise, the DNA nucleotide may be constructed by a standard method known to one skilled in the art, for example, by an automatic DNA synthesizer (available from Biosearch or Applied Biosystems). The DNA nucleotide constructed as described above is inserted into a vector containing at least one expression control sequence (e.g., promotor, enhancer, or the like) that is operatively linked to the DNA nucleotide to control the expression of the DNA nucleotide, thereby providing a recombinant expression vector, which, in turn, is used to transform a host cell. The resultant transformed cell was cultured in a suitable medium and a condition to perform the expression of the DNA sequence. Then, a substantially pure peptide encoded by the DNA nucleotide is recovered from the culture. Such recovery may be carried out by a method generally known to one skilled in the art (e.g., chromatography). As used herein, the term "substantially pure peptide" means a peptide according to the present invention does not substantially comprise any other proteins derived from a host. References to the genetic engineering method for preparing the peptide according to the present invention include: Maniatis et al., Molecular Cloning; A laboratory Manual, Cold Spring Harbor laboratory, 1982; Sambrook et al., Molecular Cloning: A Laboratory Manual, Cold Spring Harbor Press, N.Y., Second (1998) and Third (2000) Edition; Gene Expression Technology, Method in Enzymology, Genetics and Molecular Biology, Method in Enzymology, Guthrie & Fink (eds.), Academic Press, San Diego, Calif., 1991; and Hitzeman et al., J. Bio. Chem., 255: 12073-12080, 1990.

Also, the present invention provides an antibody to the bladder tumor-targeting peptide. As used herein, the term "antibody" means a specific protein molecule directed to an antigenic site. In view of the objects of the present invention, the antibody refers to an antibody that specifically recognizes the bladder tumor-targeting peptide, including a polyclonal antibody and a monoclonal antibody. As described above, since the peptide capable of specific binding to a bladder tumor cell is characterized according to the present invention, production of an antibody using the same peptide can be performed with ease according to a manner generally known to one skilled in the art (Sambrook et al., Molecular Cloning: A Laboratory Manual, Cold Spring Harbor Press, N.Y., Second (1998) and Third (2000) Edition).

The monoclonal antibody may be produced by a fusion method generally known to one skilled in the art (Kohler and Milstein (1976) *European Journal of Immunology,* 6: 511-519), a recombinant DNA method (U.S. Pat. No. 4,816,567), or by a phage antibody library method (Clackson et al., Nature, 352: 624-628, 1991; Marks et al., *J. Mol. Biol.,* 222: 58, 1-597, 1991).

Also, the polyclonal antibody may be produced by a method generally known to one skilled in the art, which comprises the steps of injecting the bladder tumor-targeting peptide having an amino acid sequence represented by SEQ ID NO: 7 into an animal, and collecting the blood from the animal to obtain blood sera comprising the antibody. For example, the peptide is injected into a goat or a rabbit along with the CFA (Complete Freund's Adjuvant) via a subcutaneous route, and then injecting a booster along with the CFA via a subcutaneous or an intraperitoneal route. Such polyclonal antibodies may be prepared from any animal hosts including a sheep, a monkey, a horse, a pig, a cow, a dog, etc., besides a goat and a rabbit.

Preferably, the antibody is labeled with a marker, for example, with a radioactive marker or a fluorescent marker. The antibody may be indirectly labeled by being conjugated with an anti-goat or anti-rabbit antibody bonded covalently to a marker compound.

The peptide according to the present invention and the antibody thereof may be used as a marker for the diagnosis of a bladder tumor. Preferably, diagnosis of a bladder tumor using the peptide according to the present invention may be carried out with ease by detecting a bladder tumor cell from the urine of a patient suspected of a bladder tumor. A bladder cell is collected from urine by centrifugation and the peptide according to the present invention is allowed to bind with the bladder cell. If the peptide according to the present invention is bonded to the bladder cell, the patient's case is diagnosed as a bladder tumor. Otherwise, it is possible diagnose of a bladder tumor by allowing the peptide according to the present invention to react with a bladder tissue or a bladder cell obtained directly from a patient suspected of a bladder tumor via biopsy, and then detecting the binding between the peptide and the tissue or the cell. To diagnose more accurately, binding of the peptide according to the present invention to a normal bladder cell as a control may be also determined. Diagnosis of a bladder tumor may be evaluated by detecting a signal capable of representing the binding of the peptide according to the present invention to the bladder tumor cell, for example, by detecting fluorescence quenching. As describe above, diagnosis of a bladder tumor according to the present invention comprising binding the bladder tumor-targeting peptide according to the present invention with a detectable label, allowing to react the labeled peptide with the bladder cell, and then detecting the signal representing the binding between the bladder tumor cell and the peptide according to the present invention to find bladder tumor cell, is more accurate than a cytology method used generally for the diagnosis of a bladder tumor cell. Furthermore, it is possible to diagnose of a bladder tumor in vivo by using the peptide according to the present invention. For example, it is possible to perform endoscopy of the bladder by labeling the peptide according to the present invention with a fluorescent material, spraying the labeled peptide into the bladder so that the peptide reacts with a bladder cell, and detecting the fluorescence. In this case, it is possible to perform diagnosis and molecular imaging of a bladder tumor more easily.

In addition to the above, the present invention also provides a kit for the diagnosis of a bladder tumor, which comprises the peptide according to the present invention. The peptide in the diagnosis kit may be prepared with ease by the method as described above. Additionally, in order to facilitate the identification, detection and determination of the polypeptide according to the present invention, bonded to the bladder tumor cell, the peptide according to the present invention may be provided in a labeled form. In other words, the peptide according to the present invention may be linked (covalently bonded or crosslinked) to a detectable label. Particular examples of the detectable label that may be used in the present invention include color developing enzymes (e.g., peroxidase, alkaline phosphatase, etc.), radio isotopes (e.g., $^{125}$I, $^{32}$P, $^{35}$S, $^{131}$I, $^{124}$I, $^{18}$F, Tc99m etc.), chromophores, light emitting materials or fluorescent materials (e.g., FITC, RITC, etc.). Similarly, as the detectable label, it is possible to use an antibody epitope, substrate, cofactor, inhibitor or affinity ligand. Such labeling work may be performed during or after the preparation of the peptide according to the present invention.

If a fluorescent material is used as the detectable material, diagnosis of a bladder tumor may be performed by an immunofluorescence staining method. For example, after the peptide according to the present invention, labeled with a fluorescent material, is allowed to react with a bladder cell, fluorescence caused by the peptide may be observed under a fluorescence microscope. If any fluorescence is observed, the bladder cell is recognized as a bladder tumor cell. Additionally, if an enzyme is used as the detectable label, absorbance is measured by the enzymatic color developing reaction of a substrate. On the other hand, if a radioactive material is used as the detectable label, radiation quantity is measured to detect a bladder tumor cell, and thus to diagnose a bladder tumor. Imaging technology for cancer diagnosis is quite advanced. Ultrasound and computed tomography (CT) equipment are commonly used to detect tumor masses. However, more advanced imaging techniques have been developed and include positron emission tomography (PET), which reveals the metabolic activity of tissues, single photon emission computed tomography (SPECT), spiral CT, magnetic resonance imaging (MRI), and endoscopic ultrasonography, which employs a fiber-optic endoscope fitted with a probe.

The kit according to the present invention may further comprise an adequate buffer or a medium for carrying out the binding between the peptide and a bladder tumor cell, and a control cell (normal bladder cell) in addition to the peptide according to the present invention. Additionally, if the peptide according to the present invention is provided in a non-labeled form, a detectable label may be further included in the kit for the purpose of labeling of the peptide. Alternatively, the kit may further comprise an antibody to the peptide according to the present invention, a secondary antibody labeled with a fluorescent material, a color developing substrate, or the like. The antibody to the peptide according to the present invention may be produced by a conventional method of producing an antibody, as described above.

Also, the peptide according to the present invention may be provided in the form of a plate whose surface is coated with the peptide. In this case, a bladder cell is inoculated directly onto the plate to perform a reaction under a suitable condition, and then the binding between a bladder tumor cell and the peptide is observed on the surface of the plate to make a diagnosis of a bladder tumor.

Experimental procedures, reagents and reaction conditions that may be used in the above methods are generally known to one skilled in the art.

Further, the present invention provides a drug delivery composition comprising the peptide according to the present invention. The peptide according to the present invention may be used as an intelligent drug carrier capable of selective delivery of a drug (such as an anti-tumor agent). If the peptide according to the present invention is linked with a conventional anti-tumor agent, it is possible to increase the efficacy of the agent and significantly reduce side effects adversely affecting normal tissue because the anti-tumor agent is delivered selectively to a bladder tumor cell by the peptide according to the present invention.

There is no particular limitation in the anti-tumor agent that may be linked with the peptide according to the present invention, and particular examples of such anti-tumor agents include cisplatin, 5-fluorouracil, adriamycin, methotrexate, vinblastine, busulfan, chlorambucil, cyclophosphamide, melphalan, nitrogen mustard, nitrosourea, or the like. Preferably, the peptide according to the present invention may be linked to an anti-tumor agent effective for the treatment of a bladder tumor. Linking of the anti-tumor agent with the peptide according to the present invention may be performed by using a conventional method generally known to one skilled in the art, including covalent bonding, crosslinking, etc. To perform this, the peptide according to the present invention may be chemically modified as long as it does not lose its activity, if desired. The amount of the peptide contained in the composition according to the present invention depends on the kind and amount of the anti-tumor agent linked with the peptide. Preferably, the peptide may be used in such an amount as to deliver the anti-tumor agent administered for the treatment of cancer to a bladder tumor tissue to a sufficient amount. However, the effective amount of a drug is determined considering various factors, including the administration route, frequency of treatment, and age, body weight, health, sex, disease severity, diet and excretion of a patient. Under these circumstances, the amount of the peptide according to the present invention, effective for treating a bladder tumor by the anti-tumor agent linked to the peptide, may be determined with ease by one skilled in the art. The composition according to the present invention may further comprise a suitable buffer solution for maintaining/preserving the stability of the peptide. There is no particular limitation in the form, administration route and administration mode of the drug delivery composition comprising the peptide according to the present invention, as long as the composition provides a desired effect. For example, the peptide according to the present invention may be administered via an oral route or a parenteral route. In the case of oral administration, the peptide according to the present invention is preferably mad up with L-type amino acids in order to prevent its decomposition due to digestive enzymes present in the gastrointestinal duct. The perenteral administration routes include subcutaneous injection, intramuscular injection, intravenous injection, urethral introduction, etc., and intravenous injection or urethral introduction is preferred.

In addition, the composition according to the present invention may further comprise pharmaceutically acceptable carriers that are added conventionally to a general pharmaceutical composition. The term "pharmaceutically acceptable" refers to carriers that are physiologically acceptable and cause no allergic reactions or similar reactions, such as gastrointestinal disorders or fainting, when administered to a human or an animal. In the case of injection formulation, particular examples of the pharmaceutically acceptable carriers include a buffering agent, a preserving agent, an anesthetic agent, a solubilizing agent, an isotonic agent and a stabilizer. As mentioned above, the composition comprising the peptide according to the present invention may be formulated in various forms. For example, an injection formulation may be provided in a unit dose ample or a multidose vial. The drug delivery composition comprising the peptide according to the present invention may be administered via a conventional route generally known to one skilled in the art.

BEST MODE FOR CARRYING OUT THE INVENTION

Hereinafter, the present invention will be described in detail by examples. It will however be obvious to a person skilled in the art that the present invention is not limited to or by the examples.

Example 1

Selection of Peptides Capable of Specific Binding to Bladder Tumor Cells

<1-1> Production of Phage Peptide Library

To search out peptides specific to bladder tumor cells, the phage peptide display technique was used (Smith, Science, 228: 1315-1317, 1985). The phage peptide display technique comprises displaying a peptide consisting of several amino acids or several tens of amino acids on the surface of a bacteriophage. The phage peptide display technique is very useful for searching out a peptide capable of targeting a desired tissue or tumor by screening many kinds of peptides at the same time, because it enables production of a phage library having $10^9$ kinds of peptides to the highest degree.

To produce a phage peptide library for the purpose of screening of peptides specific to bladder tumor cells, oligonucleotides, which encode CX7C peptides having cysteins at both ends and containing optional seven amino acids between both ends, were randomly synthesized. The above synthesis for oloigonucleotides was performed by Invitrogen Co. (Carlsbad, Calif., USA). Then, the oligonucleotides were cloned into the protein genes forming the surface of the T7 415-1b phage by using the T7Select® phage cloning kit available from Novagen Co. to produce a phage peptide library. The phage peptide library obtained as described above was measured for its diversity and was shown to have a diversity of about $5 \times 10^8$ pfu.

<1-2> Screening of Phage Library

HT-1376 human bladder tumor cells (American Tissue Culture Collection Co.) were transplanted into the subcutaneous layer of a Balb/c nude mouse (Hyochang Science) to induce a tumor. The tumor tissue from the mouse was cut and pulverized finely to provide a cell suspension. Next, the tumor cell suspension was allowed to react with magnetic beads (Dynal Co.) coated with an antibody to epithelial cells at 4° C. for 30 minutes to perform the binding of the tumor cells to the magnetic beads. Then, the magnetic beads were mixed with the cell suspension separated from the normal bladder in order to remove phages capable of binding to normal epithelial cells, i.e., phages non-specific to the bladder tumor cells. After this, the magnetic beads were added to the phage library obtained from Example <1-1> and allowed to react with the phage library at 4° C. for 2 hours. After the completion of the reaction, tumor cells, to which the magnetic beads were bonded, were separated by using a magnet. Herein, because the epithelial cells separated from the normal bladder were not preliminarily bonded to the magnetic beads, they could not be separated by the magnet. The tumor cells separated as described above were treated with a lysis buffer based on Triton-X 100 to detect phages bonded to the cells. A part of the phages was measured for the titer according to a method known to one skilled in the art, and the remaining part thereof was amplified and subjected to four rounds of re-detection of phages capable of binding to tumor cells (see FIG. 1). As can be seen from FIG. 1, the phage titer was increased significantly after the second screening round, and showed no significant difference after the second round. This indicates that screening of phages was successful.

Then, 96 clones among the screened phages were measured for the binding capability to cultured tumor cells using the ELISA method. First, $3 \times 10^4$ HT-1376 human bladder tumor cells were transplanted into a cell culture container (96 wells), cultured for 16 hours, and then were allowed to conjugate with $1 \times 10^{10}$ pfu phages at 4° C. for 1 hour. Herein, the normal renal cells of the NRK mouse (American Tissue Culture Collection Co.) were used as a control. Then, antibodies for the phages (Novagen Co., 1:3000 dilution) linked with color developing enzymes were added to each well to perform a reaction at room temperature for 1 hour. After this, a color developing agent (TMB, Pierce) was added thereto to perform a reaction for additional 30 minutes. Upon the quenching of the reaction, the reaction mixture showed a yellowish brown color, and then the color developing degree was measured by using a reader for ELISA. In general, as the number of phages conjugated with the cells increases, the color developing degree also increases. As a result, 20 phage clones having a relatively high binding capability to the HT-1376 bladder tumor cells, as compared to the normal renal cells of the NRK mouse, were selected (data not shown).

<1-3> Reading of Base Sequence of Positive Phage Clones and Amino Acid Sequencing To determine which peptide was displayed on the 20 phage clones selected from Example <1-2>, DNA inserted into the phages was amplified by PCR amplification and sequenced. Herein, primers represented by SEQ ID NO: 8 and SEQ ID NO: 9 were used. PCR was performed by the steps of: pre-denaturating a template DNA at 95° C. for 5 minutes; 35 cycles at 94° C. for 50 seconds, at 50° C. for 1 minute and at 72° C. for 1 minute; and extending at 72° C. for 6 minutes.

Next, the base sequence of the PCR product was read by a base sequence analyzer (Bioneer). Amino acid sequence was deduced based on the base sequence. After analyzing the deduced amino acid sequence by using the Clustal W program, a consensus sequence of CXNXDXRXC (SEQ ID NO: 7) was found, as shown in FIG. 2. Peptides of typical six clones were represented by SEQ ID NO: 1 to SEQ ID NO: 6.

Example 2

Analysis for Binding Capability of Peptide of the Present Invention to Bladder Tumor Cell <2-1> Analysis for Binding Capability of Six Phage Clones Bladder tumor cells were separated from fresh bladder tumor tissue obtained from six patients with a bladder tumor by transurethral resection of bladder tumor, according to a known method. The cells were measured for the specific binding of the six individual phage clones (SEQ ID NO: 1 to SEQ ID NO: 6) described in Example 1 to the tumor cells and compared their binding to that of the normal cells. First, bladder tumor tissue and normal bladder tissue were pulverized finely to provide cell suspensions, and the six phages ($5 \times 10^9$ pfu) were allowed react with the cells at 4° C. for 2 hours. A non-recombinant phage, T7 415-1b phage, was used as a control phage. Next, tumor cells and the normal epithelial cells were separated from the cell suspensions formed from the tumor tissue and the normal tissue by using magnetic beads coated with epithelial cell antibodies, in the same manner as described in Example <1-2>. Then, phages were detected from the cells and measured for the titer of phages, in the same manner as described in Example <1-2>.

As shown in FIG. 3, six phage clones selected from Example 1 showed excellent specificity to tumor cells.

<2-2> Peptide Synthesis and Analysis for its Binding Capability to Bladder Tumor Tissue First, peptide 1 (SEQ ID NO: 1), which showed the highest binding capability among the six phage clones selected in Example 1, was synthesized by a peptide synthesis specialist (Anigen) to a purity of 85% or higher. Herein, a green fluorescence material, FITC (fluorescein isothiocyanate), linked to its amino terminal of the peptide.

To examine whether the peptide according to the present invention was bonded specifically to bladder tumor cells, bladder tissue of a normal human, bladder tissue obtained from a patient by transurethral resection of bladder tumor, and lung cancer tissue were subjected to frozen biopsy to provide slides. Next, 10 μM of the peptide, FITC-CSNRDARRC, was allowed to react with the tissues at 4° C. for 1 hour. As a control, a peptide (SEQ ID NO: 10; CDASRRNRC), which had the same number of amino acids as the peptide according to the present invention but included a randomly modified amino acid sequence between both terminal cystein residues, was used. After the reaction of each peptide, a mounting solution (molecular Probe) containing a nucleus staining reagent, DAPI (4',6-diamidino-2-phenylindole), was treated on the surface of the slide according to the method known to one skilled in the art. Then, the slide was observed by using a fluorescence microscope.

As shown in FIG. 4, the FITC-peptide 1 was bonded specifically to bladder tumor tissue. On the contrary, the control peptide substantially showed no binding to bladder tumor tissue.

Example 3

In Vivo Bladder Tumor Cell Targeting of Peptide According to the Present Invention <3-1> Preparation of Bladder Tumor Model Mouse First, 4 week-aged F344 rats (n=10) (Hyochang Science) were fed with water containing 0.05% of N-butyl-N-4-hydroxybutylnitrosoamine (BBN) for 8 weeks to induce a bladder tumor.

<3-2> Injection of Peptide According to the Present Invention Via Urethra

50 μM of FITC-CSNRDARRC peptide described in Example <2-2> was injected into the bladder of each of the mouse, in which a bladder tumor was induced, and a normal mouse via the urethra, followed by reaction for 30 minutes. Then, the bladder was removed from each mouse and a frozen section was provided. The frozen section was stained by H&E staining according to a method known to one skilled in the art. Additionally, in order to stain the epithelial cells of the bladder tissue, 1:1000 dilution of a CK18 antibody (Molecular probe), which is one of cytokeratines, was allowed to react with the frozen section at room temperature for 1 hour. Then, 1:200 dilution of a secondary antibody, to which a red fluorescence material (Alexa red) was bonded, was allowed to react with the cells at room temperature for 1 hour, followed by treatment with a mounting solution containing DAPI. Next, the cells were observed by using a fluorescence microscope.

As shown in FIG. 5, a green fluorescence was observed in the epithelial cells at the site, in which a bladder tumor was induced, due to the binding of the peptide according to the present invention. However, no fluorescence was observed in the epithelial cells covering the normal bladder.

<3-3> Injection of Peptide According to the Present Invention into Blood

The FITC-peptide 1 was injected into the mouse, in which a bladder tumor induced, and into the normal mouse via the tail venous to a final concentration of 50 μM in the blood, followed by circulation for 2 hours. Additionally, to determine whether the peptide according to the present invention specifically targets the bladder tumor in vivo, a malignant melanoma was induced in a mouse (Hyochang Science), and the peptide according to the present invention was injected into the mouse in the same manner as described above. Then, the bladder was removed from each mouse to prepare a frozen section, which, in turn, was stained by H&E staining or cytokeratin staining. Each section was observed by using a fluorescence microscope.

As shown in FIG. 6, the peptide according to the present invention targets the bladder tumor cells even when it is injected into the blood. However, the peptide according to the present invention was not detected in the normal bladder cells, lung tissue of a normal mouse and malignant melanoma tissue. The distribution of the peptide observed in the bladder tumor cells was similar to that of cytokeratin as an epithelial cell protein.

Example 4

Diagnosis of Bladder Tumor Using Peptide According to the Present Invention

Urine of a patient that was in the hospital for surgical operation on the bladder tumor was centrifuged with 1500 rpm at 4° C. for 10 minutes to collect cells. As a control, bladder cells, collected from the urine of a normal human in the same manner as described above, were used. Next, the collected cells were allowed to react with the FITC-peptide 1 described in Example <2-2> and the control peptide (SEQ ID NO: 10) at 4° C. for 1 hour. After staining the cells with DAPI, the cells were transferred onto a slide and observed with a fluorescence microscope. Meanwhile, the cells were stained with the PAP staining method (Papanicolau and Marshall, Science 101:519, 1945), currently used as a method for the diagnosis of bladder tumor, to observe the presence of tumor cells.

As shown in FIG. 7, in the cells of the patient suffering from bladder tumor, a green fluorescence was observed due to the binding of the CSNRDARRC peptide (SEQ ID NO:10) according to the present invention. However, in the control cells, fluorescence was not detected. Additionally, it was also found that tumor cells were present in the patient cells according to the PAP staining method. However, in the case of the control peptide, it was found that the peptide could not be bonded with the cells of the patient suffering from bladder tumor. As compared to the results obtained from the conventional PAP staining method, the peptide according to the present invention permits more rapid and more convenient diagnosis of bladder tumor by virtue of the use of fluorescence. In other words, the peptide according to the present invention provides excellent sensitivity compared to the cytology diagnosis using the PAP method, which shows the problems of low sensitivity or detectability. However, because the cytology diagnosis has higher diagnostic specificity or accuracy, both techniques may be utilized in combination to provide ideal results.

Example 5

Examination of Bladder Tumor Cell Targeting of Peptide According to the Present Invention Using Pet For radioiodination, each of CSNRDARRC peptide (SEQ ID NO: 1) and CDASRRNRC control peptide (SEQ ID NO: 10) was added with a tyrosine residue at the N-terminus during synthesis. The peptide is cyclized through disulfide bond using two cysteine residues at C- and N-termini, which is expected to make a peptide more stable in physiological condition. The synthetic peptide was labeled with [131I]NaI by using Iodo-bead (Pierce Biochemical Co., Rockford, Ill.). The bead was washed with phosphate-buffered saline (PBS), pH 7.2 and dried on filter paper for 5 min. The washed bead was added to a solution of [131I]NaI (100 MBq) in PBS. After shaking at RT for 5 min, the peptide solution (14 mg in 20 mL distilled water) was added to the [131I]NaI solution containing Iodo-bead. [131I]NaI (T1/2=8.6 days) was purchased from Korea Institute of Radiology and Science (KIRAMS; Seoul, Korea). The reaction was allowed to proceed for 15 min at RT by gentle shaking and then stopped by the removal of the bead out of the reaction tube. The 131I-incorporation yield measured by radio-TLC was 47% (silica, 10% ammonium acetate:methanol=30:70). The 131I-labeled peptide was purified by HPLC with Shiseido Capcell Pak C-18 column (3 mm, 4.6×50 mm) and gradientsolvents of 0.1% trifluoroacetic acid (TFA) in distilled water (Solvent A) and 0.1% TFA in acetonitrile (solvent B) (Solvent A:solvent B=97:3 20:80 over 30 min) at flow rate of 1 mL/min. The collected peptide (30.6 MBq) was concentrated completely, and then redissolved in saline for animal injection. The radiochemical purity of final solution was measured to be over 81.2%. The [124I]-labeled peptide was intravenously administered into three F344 rats bearing BBN-induced tumor prepared in the same manner as described in Example <3-1>.

As shown in FIG. 8, when in vivo micro PET images were taken at 14 hours after injection of a peptide into the tumor-bearing rats, strong uptake of the [124I]-labeled peptide 1 (380 μCi) was observed (FIG. 8 A-C). In contrast, uptake of the control peptide (313 μCi) was minimal (FIG. 8 D-F). These findings indicate that the radioactivity shown in rat bladder is not a non-specific one from urinary excretion of the radiolabeled peptides but a specific one from the uptake of the peptide by bladder tumor tissues.

INDUSTRIAL APPLICABILITY

As described above, the peptide according to the present invention is very useful for the diagnosis of bladder tumor. Diagnosis of bladder tumor using the peptide according to the present invention or an antibody thereof permits more convenient and more accurate diagnosis of bladder tumor compared to conventional methods for the diagnosis of bladder tumor. Additionally, combination of the method for the diagnosis of bladder tumor according to the present invention with a conventional method for the diagnosis of bladder tumor is very effective for the early diagnosis of bladder tumor and early detection of recurrence of bladder tumor after operation. Further, the peptide according to the present invention may be useful for a drug carrier. In other words, when the peptide according to the present invention is linked to a drug such as an anti-tumor agent and used for therapy, it is possible to deliver the drug selectively to bladder tissue, and thus to increase the drug efficacy and to reduce side effects.

What is claimed is:

1. An isolated peptide that targets bladder tumor cells, which comprises an amino acid sequence represented by the formula:

Cys Xaa Asn Xaa Asp Xaa Arg Xaa Cys   (SEQ ID NO: 7);

wherein,
- the second amino acid (Xaa) is selected from the group consisting of serine (S), proline (P), alanine (A) and valine (V);
- the fourth amino acid (Xaa) is selected from the group consisting of arginine (R), glycine (G), lysine (K), glutamine (Q), asparagine (N) and leucine (L);
- the sixth amino acid (Xaa) is selected from the group consisting of alanine (A), glutamic acid (E), valine (V), serine (S), glutamine (Q) and threonine (T); and
- the eighth amino acid (Xaa) is selected from the group consisting of arginine (R), asparagine (N) and leucine (L).

2. The peptide according to claim 1, wherein the amino acid sequence is SEQ ID NO: 1.

3. A kit for diagnosis of bladder tumor, which comprises the peptide as defined in claim 1.

4. The kit according to claim 3, wherein the peptide is labeled with a fluorescent material.

5. A drug delivery composition, which comprises the peptide of claim 1 and a drug.

6. The drug delivery composition according to claim 5, wherein the drug is an anti-tumor agent.

7. The peptide according to claim 1, wherein the amino acid sequence is any one selected from the group consisting of amino acid sequences represented by SEQ ID NO: 2 to SEQ ID NO: 6.

8. The kit according to claim 3, wherein the peptide is labeled with any one selected from the group consisting of a color developing enzyme, a radioactive isotope, a chromophore, and a light emitting material.

* * * * *

SEQUENCE LISTING

```
<160> NUMBER OF SEQ ID NOS: 10

<210> SEQ ID NO 1
<211> LENGTH: 9
<212> TYPE: PRT
<213> ORGANISM: Artificial
<220> FEATURE:
<223> OTHER INFORMATION: Bladder Tumor-Targeting Peptide 1

<400> SEQUENCE: 1

Cys Ser Asn Arg Asp Ala Arg Arg Cys
1               5

<210> SEQ ID NO 2
<211> LENGTH: 9
<212> TYPE: PRT
<213> ORGANISM: Artificial
<220> FEATURE:
<223> OTHER INFORMATION: Bladder Tumor-Targeting Peptide 2

<400> SEQUENCE: 2

Cys Pro Asn Gly Asp Glu Arg Asn Cys
1               5

<210> SEQ ID NO 3
<211> LENGTH: 9
<212> TYPE: PRT
<213> ORGANISM: Artificial
<220> FEATURE:
<223> OTHER INFORMATION: Bladder Tumor-Targeting Peptide 3

<400> SEQUENCE: 3

Cys Ala Asn Lys Asp Val Arg Arg Cys
1               5

<210> SEQ ID NO 4
<211> LENGTH: 9
<212> TYPE: PRT
<213> ORGANISM: Artificial
<220> FEATURE:
<223> OTHER INFORMATION: Bladder Tumor-Targeting Peptide 4

<400> SEQUENCE: 4

Cys Pro Asn Gln Asp Ser Arg Arg Cys
1               5

<210> SEQ ID NO 5
<211> LENGTH: 9
<212> TYPE: PRT
<213> ORGANISM: Artificial
<220> FEATURE:
<223> OTHER INFORMATION: Bladder Tumor-Targeting Peptide 5
```

```
<400> SEQUENCE: 5

Cys Val Asn Asn Asp Gly Arg Leu Cys
1               5

<210> SEQ ID NO 6
<211> LENGTH: 9
<212> TYPE: PRT
<213> ORGANISM: Artificial
<220> FEATURE:
<223> OTHER INFORMATION: Bladder Tumor-Targeting Peptide 6

<400> SEQUENCE: 6

Cys Ala Asn Leu Asp Thr Arg Arg Cys
1               5

<210> SEQ ID NO 7
<211> LENGTH: 9
<212> TYPE: PRT
<213> ORGANISM: Artificial
<220> FEATURE:
<223> OTHER INFORMATION: Bladder Tumor-Targeting Peptide 7
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 7

Cys Xaa Asn Xaa Asp Xaa Arg Xaa Cys
1               5

<210> SEQ ID NO 8
<211> LENGTH: 20
<212> TYPE: DNA
<213> ORGANISM: Artificial
<220> FEATURE:
<223> OTHER INFORMATION: Forward Primer for PCR

<400> SEQUENCE: 8
agcggaccag attatcgcta                                              20

<210> SEQ ID NO 9
<211> LENGTH: 20
<212> TYPE: DNA
<213> ORGANISM: Artificial
<220> FEATURE:
<223> OTHER INFORMATION: Reverse Primer for PCR

<400> SEQUENCE: 9
aacccctcaa gacccgttta                                              20

<210> SEQ ID NO 10
<211> LENGTH: 9
<212> TYPE: PRT
<213> ORGANISM: Artificial
<220> FEATURE:
<223> OTHER INFORMATION: Control Peptide
```

-continued

```
<400> SEQUENCE: 10

Cys Asp Ala Ser Arg Arg Asn Arg Cys
1               5
```